United States Patent [19]

Vaillancourt

[11] Patent Number: 4,904,248

[45] Date of Patent: Feb. 27, 1990

[54] FEMALE INCONTINENT URINE COLLECTION DEVICE

[75] Inventor: Vincent L. Vaillancourt, Livingston, N.J.

[73] Assignee: Sherwood Medical Company, St. Louis, Mo.

[21] Appl. No.: 13,638

[22] Filed: Feb. 11, 1987

Related U.S. Application Data

[63] Continuation-in-part of Ser. No. 830,362, Feb. 18, 1986, abandoned.

[51] Int. Cl.⁴ ............................................... A61M 1/00
[52] U.S. Cl. ..................................... 604/329; 604/327
[58] Field of Search ............... 604/128, 129, 326, 327, 604/328, 329, 330, 337, 345, 346, 347, 348, 349, 350, 351, 352, 353; 128/760, 761, 767

[56] References Cited

U.S. PATENT DOCUMENTS

| | | | |
|---|---|---|---|
| 3,194,238 | 7/1965 | Breece, Jr. | 604/329 |
| 3,820,546 | 6/1974 | Chittenden et al. | 604/326 |
| 3,964,111 | 6/1976 | Packer | 4/144.4 |
| 4,194,508 | 3/1980 | Anderson | 604/329 |
| 4,202,058 | 5/1980 | Anderson | 604/347 |
| 4,257,422 | 3/1981 | Duncan | 604/282 |
| 4,496,355 | 1/1985 | Hall et al. | 4/144.3 |
| 4,681,572 | 7/1987 | Tokarz et al. | 128/761 |

FOREIGN PATENT DOCUMENTS

| | | | |
|---|---|---|---|
| 774905 | 1/1968 | Canada | 128/761 |
| 2101881 | 8/1971 | Fed. Rep. of Germany | 604/350 |
| 2339614 | 3/1974 | Fed. Rep. of Germany | 604/129 |
| 2817571 | 10/1978 | Fed. Rep. of Germany | 604/329 |
| 1193261 | 5/1970 | United Kingdom | 604/329 |

*Primary Examiner*—Stephen C. Pellegrino
*Attorney, Agent, or Firm*—Kenyon & Kenyon

[57] ABSTRACT

This invention pertains to both an apparatus and a method for constructing and using an incontinent female urine collection device. A molding of a partly resilient material and having a cup-shape and a stepped bore in said receptacle, is provided. Several attachment configurations to receive and retain a resilient, soft, compliant outer-rim portion are shown. This rim portion is secured to a lip edge of the molding by adhesive and the like to provide a fluid-tight seal when this device is mounted in the folds of the user's labia. A first length of tubing is secured in a formed stepped bore as by adhesive and/or the like. The discharge end of this tubing is connected to a second tubing conductor leading to a urine collection receiver. A vent in this conductor is provided to prevent air binding. A panty garment having elasticized properties is made with a reinforced aperture sized to accept and retain the first length of discharge tubing. This reinforcement is adapted for resisting wear, raveling and enlargement. The resilient, compliant rim provides a soft, non-irritating fluid-tight seal of the worn collection device to the skin area of the female labia. The receptacle and rim portion thereof may be integrally formed of closed cell silicone foam.

15 Claims, 2 Drawing Sheets

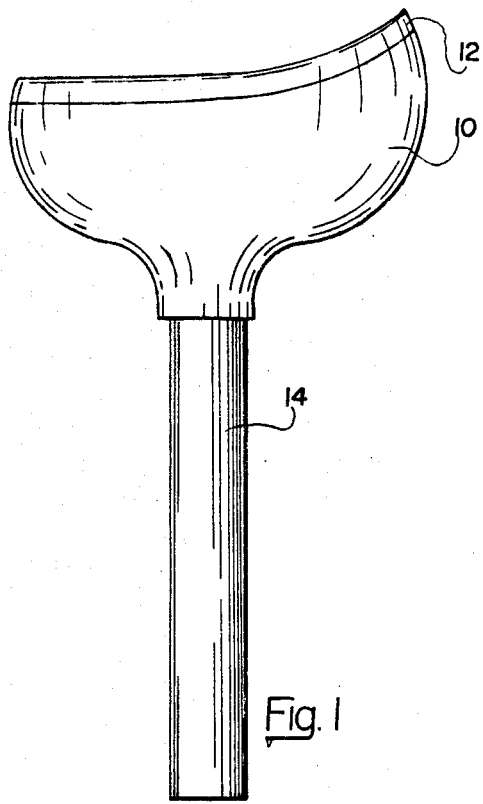
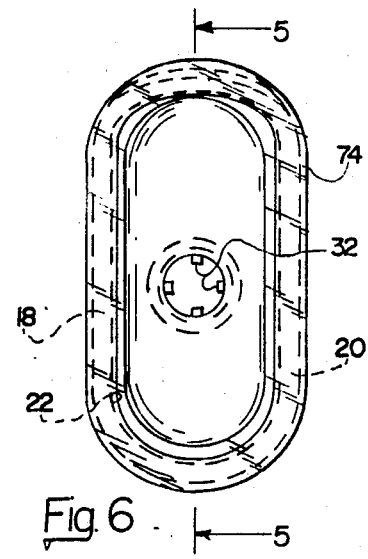
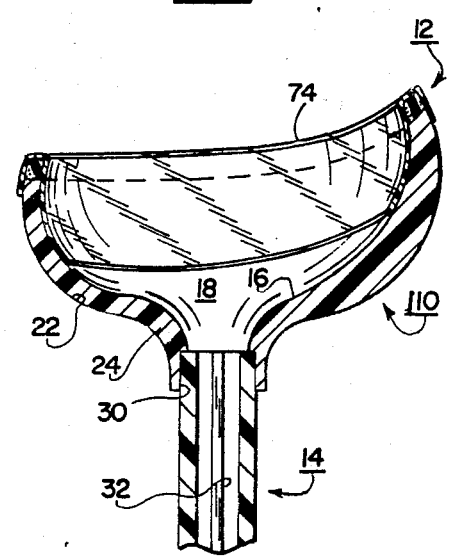
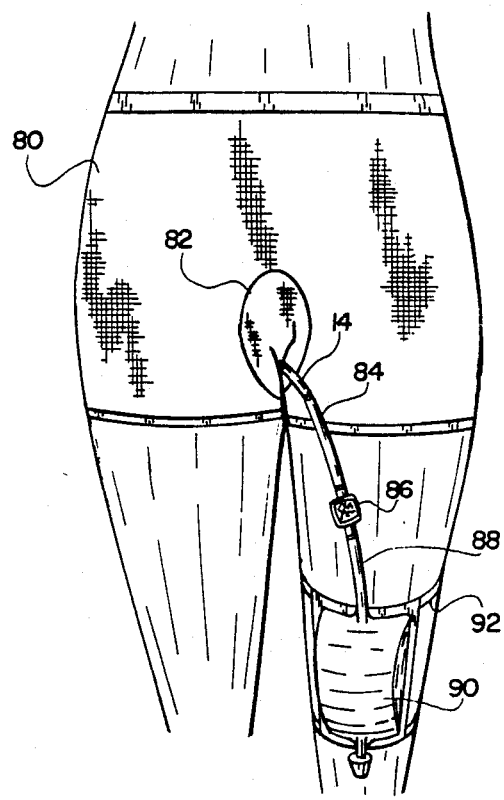
Fig. 1
Fig. 6
Fig. 5
Fig. 7

FEMALE INCONTINENT URINE COLLECTION DEVICE

CROSS-REFERENCE TO RELATED APPLICATION

This is a continuation-in-part of U.S. patent application Ser. No. 830,362, filed Feb. 18, 1986 now abandoned.

FIELD OF THE INVENTION

This invention relates a female incontinent urine collection device and, in particular, to urinary appliances for conducting urine from the patient to a collection bag or pouch. In particular, this device is for the use of and by females where and when the subject is walking, sitting upright or in a generally reclining position.

DESCRIPTION OF THE PRIOR ART

Urinary collection devices for both male and female patients are known and have been the subject of many patents. Commerical devices are well known, including catheters, among which is the "Foley." The "Foley" is an internal drainage device which is used by women, but with prolonged use becomes uncomfortable, may cause irritation, and is prone to infecting the patient. Hence, unless absolutely necessary, most hospital protocols dictate their removal after 3-5 days. External drainage devices for males generally include securing in one form or the other around the male organ. Among the well known devices is that known as the "Texas Catheter." As far as is known and prior to this invention, a generally acceptable device for an incontinent female patient's use was not available except those custom-made.

Females who are incontinent often resort to diapers, artificial sphincters or, as previously mentioned, custom-made devices. Except for diapers, these devices are expensive and may require surgical procedures. Diapers have the disadvantage that no means is provided to convey the urine away from the site. Urine collection devices may be required due to inoperative or leaking sphincters, loss of bladder control, or due to neurological or physical damage, among other reasons.

Female appliances for collecting and conducting urine through a tube to a receptacle are well known. Such appliances when conventionally positioned and worn usually leak when movement occurs. Custom-made devices worn with a securement harness are claimed to avoid this problem. These appliances when and as retained by a securement harness need to be tightly positioned to effect a non-leak condition and as such are uncomfortable. Known prior art devices when used with a securement harness may bind, pinch or irritate the patient.

The leakage problem, above noted, is addressed in the U.S. Pat. No. 4,496,355 wherein a receiver cup is custom-formed (usually by molding), with inner and outer configurations made to tightly conform to this particular female human form. Much of the other prior art has not addressed this leakage problem which is caused or associated with bodily engagement of the device upon a particular human form. Many, if not all, the prior art devices except the patent, identified above, have avoided discussion of a leak-free female urinary incontinent device. Most prior art patents and commerically produced products pertain to female urinals which are designed for external fit to that area around the vulva.

The essential element to providing a leak-free device for a female urinary problem is in the way in which said device conforms to the individual female human anatomy. Many of the difficulties associated with making female incontinent urine collection devices leak-proof or substantially leak-proof for use in a universally applicable product are due to variations in the female anatomy. The female organs in the external configuration are unique to each female and the mons veneris, in particular, presents difficulties in retaining a formed cup. The labia (majora and minora), although a skin, is adapted for a moist condition. This labia skin area surrounding the female orifice (urethra) is very sensitive and is easily irritated when a device is not fitted properly. Custom molding of a fitted device is not only initially expensive, but through continued wearing of said device may become worn to the extent of requiring repair or replacement. The molded appliance, noted above, provides double sealing surfaces, custom-made, and generally elliptical with a generally convex shape. This patent has the outer seal portion adapted to provide an external fit of the device. Many, if not all, previously known urine collection devices for use by and for females include removable construction with retention by an adjustable strap harness means. Among the prior art devices is ANDERSON, U.S. Pat. No. 4,202,058, as issued May 13, 1980, which is a cup-shaped urinal designed to engage the body parts surrounding the vulva. Another urine collection apparatus is shown in the U.S. Pat. No. 4,270,539 to MICHAUD, as issued June 2, 1981. This apparatus also is directed to bringing a device against the user's body and provides an external fit. Another device is shown in U.S. Pat. No. 4,421,511, issued to STEER et al on Dec. 20, 1983, which is designed to fit to the user's anatomy external to the labia majora.

The collection device of this invention is believed to be a novel and distinct improvement over the known prior art devices. This collection device is to be worn by the user and carried within the labia area. The retention of this novel incontinent female collection device by and with a panty or panty-girdle with a reinforced aperture is also believed to be novel.

SUMMARY OF THE INVENTION

This invention may be summarized, at least in part, with reference to its objects. It is an object of this invention to provide, and it does provide, an incontinent female collection device which has a molded cup receptacle and an attached rim that is soft and compliant. This device in a worn condition provides a leak-free sealing engagement with the labia skin tissue of the user.

It is a further object to provide, and it does provide, an incontinent female collection device which is not only leak-free, but in use has a minimum and relatively minor degree of discomfort.

Another object of this invention is to provide, and it does provide, a nearly "universal" device or product which is contemplated to be made in a limited number of sizes and therewith satisfy a significant portion of the female users. This collection device is not a custom-made product.

In brief, this collection device is used with a female patient and, when worn, is adapted to sealingly engage the female anatomy (form) in the labia skin tissue at and around the female organ. This device, when secured and used by a patient, collects urine from the patient in a continuous or semi-continuous manner. This discharge is conducted through a tube to a collection container retained by a leg strap or like means. When filled, the collection container is emptied or discarded.

The female incontinent device of this invention consists of a molded cup which provides the intermediate reservoir or catch container for a female void. The base of the molded cup is formed to receive and retain a non-kinking drain tube which is also fluid-connected to a collection container. A vent prevents a negative pressure build-up in the discharge system. To the top of this molded cup edge is secured (usually integrally molded) a soft, complaint foam rim which readily compresses to the female patient's anatomy. This foam resilient rim portion provides a seal by conforming to the "hills and valleys" of the patient's labia and applies substantially uniform pressure to minimize "pressure points," irritation, etc., should the collection device and/or the securement accessory move slightly. This resilient foam rim compensates for any changes that may occur. This foam rim attached to and extending from the molded cup is made sufficiently soft so as to accommodate most, if not all, female users. The labia skin area of the female user is quite sensitive so the contact portion must be soft so as not to irritate the female user.

The female urinals which are designed to fit externally around the vulva present problems in use. These urinals are provided with strapping means which are contemplated to hold these devices to the user's skin. These urinals have those areas interior of the cup-shaped retainer exposed to urine. The mons veneris area is a skin area usually and conventionally exposed to atmosphere and, in the absence of a urinal, is therefore accustomed to a dry environment. When the urinal is strapped in place, this area interior of the rim is now continuously subjected to be fluid-bound with urine. Such skin becomes excoriated, irritated, tender, etc. The external skin is not meant to be in contact with urine or a moist atmosphere and does not adapt to such a condition.

The foam compliant sealing means as used with the molded cup device is attached by a selected configuration, to be more particularly shown and described hereinafter. Although the female anatomy is in many shapes and sizes, it is contemplated that a number of sizes be made as a mass-produced product and, after a patient is fitted (measured for a particular cup size), she may obtain additional units by specifying the selected size. The foam compliant sealing means may be provided as a unitary molding of foam rubber or plastic.

The present invention is designed to provide a compliant rim for the collection device so a fluid-free seal is provided when positioned within the folds of the labia and held in place, using an appliance that applies pressure to the urine collection device. It is also to be noted that a molding of foam rubber may be provided where the rim area is made of sufficient softness to avoid discomfort to the wearer. The sealing compliant rim is adapted to engage the labia skin area of the patient so that the orifice of the urethra is open to the cup interior of the device. The molded shape of the device is of rubber or plastic and has sufficient rigidity so as to retain the molded shape and prevent deformation of the cup shape and the tubular discharge conductor. This conductor is provided with an anti-kink configuration and means. This cup-shaped molding in and of itself is more stiff or rigid to provide a non-collapsing shape. A very soft, compliant rim portion is needed and provided to present the fluid seal and a non-irritating fit of the worn device to the labia of the user.

As to be more fully shown and described, the molding may be of plastic, rubber or rubber-like material that is partially resilient for comfort in placement and use. This molding is contemplated to be made in a plurality of sizes, with each molding fitted with an added very soft, compliant rim portion of foam rubber or plastic. This rim material is contemplated to be about one-eighth to one-quarter inch in protrusion and may be secured to the molding edge by adhesive, insert molding or a retaining means such as a groove. This rim portion is made of a material having an apparent hardness of thirty-five Durometer on the "A" scale, which is comparable to soft foam rubber. The foam material for this rim is of a non-setting composition and, while soft, must be non-irritating and compatible with securing procedures. Among the several embodiments there is shown a very thin liner which protects the foam from urine which, after a period of time, develops an odor. In this manner, the liner may prolong the useful life of the device before replacement is required. It is also to be noted that a molding of foam rubber may be provided where the rim area is made of sufficient softness to avoid discomfort to the wearer.

It is contemplated that the entire device, except for the tubing conductor, may be made of a molded material such as a suitably soft, closed-cell silicone foam. The cup portion is thicker than the contacting rim portion so that this thicker (cross-section) portion is resistant to collapsing during wearing use. This closed-cell foam silicone material provides a soft contact in and with the molded cup. This soft rim achieves the desired seal. The panty supplies the needed and necessary strength to prevent the product from being yanked (pulled) out inadvertently or otherwise.

This urine collection device and the secured-in-place compliant rim portion is brought to the user with the upward curved portion in the upward position when fitted with the urine-receiving cavity of the device in position to receive the flow of urine from the urethral orifice of the patient. This compliant rim provides and is enhanced by the configuration in which the frontal shape of the molding matches in general the angle and body surfaces of the female labia fold area of the user. The very soft rim material accommodates and matches this frontal labia fold configuration of the user, which shape has minor or subtle changes daily, if not hourly. The attempt to exactly or very closely match the contour of a patient or user by a molding is often unsatisfactory or, in trying to match the two level contours as in U.S. Pat. No. 4,496,355, is or becomes irritating for the reasons above.

As to be more fully described, the molding is of plastic or rubber, generally saddle-shaped, with a wall thickness sufficient to prevent deformation in use. A tubular conduit extends from the cavity and is adapted to be connected to a bag retainer. The molded receptacle and the hollow stem portion are usually unitarily molded, with the compliant rim portion additionally secured. The molded cavity and stem are essentially symmetrical about a central portion, with the larger portion of the molding having a generally egg-shaped or ovoid outer perimeter which is generally elliptical. Rather than molded surfaces, the soft rim forms a continuous sealing, generally convex surface. This compliant surface provides a saddle configuration adapted to mate with the female form of the fold area of the user's labia.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of a female urinary collection device as adopted for use with a female human user and showing a preferred means for constructing and using said device. This specific embodiment has been chosen for the purpose of illustration and description as shown in the accompanying drawings wherein:

BRIEF DESCRIPTION OF THE DRAWINGS

FIG. 1 represents a side view of a female urinary collection device of this invention;

FIG. 4A through FIG. 4G represent fragmentary, enlarged sectional views showing methods of attaching a compliant rim structure to the top edge of the collection device wherein;

FIG. 4A represents the fragmentary, enlarged view of the compliant rim attached by adhesive to the top edge of the molded cup;

FIG. 4B represents a fragmentary, enlarged view similar to that of FIG. 4A as attached by adhesive, but with the compliant rim formed with a V-groove and with the molded cup formed with a compatible edge configuration;

FIG. 4C represents a fragmentary sectional view in an enlarged scale similar to the showing in FIG. 4B, but showing a reverse arrangement of the mating alignment configuration of the rim to the lip edge of the molded receptacle;

FIG. 4D represents the fragmentary, enlarged view of FIG. 4A, but with the compliant rim formed with a locking mortise and tennon structure and with the molded edge with a compatible female groove;

FIG. 4E represents a fragmentary sectional view in an enlarged scale similar to the showing in FIG. 4D, but showing a reverse arrangement of the mating alignment configuration of the rim to the lip edge of the molded receptacle;

FIG. 4F represents a fragmentary enlarged view with a hollow compliant rim and with a protruding bead portion sized to be received and retained in a compatible groove formed in the edge of the molded collection device;

FIG. 4G represents a fragmentary sectional view in an enlarged scale similar to the showing in FIG. 4F, but showing a reverse arrangement of the mating alignment configuration of the rim to the lip edge of the molded receptacle;

FIG. 5 represents the collection device of FIG. 2 with an additional very thin liner disposed to provide resistance to urine;

FIG. 6 represents the plan view of the device of FIG. 5, and

FIG. 7 represents a diagrammatic face view of the device in a use condition and secured with and by an elasticized panty or panty pad and providing a reinforced aperture and an additional conductor means to a vent and a collection container.

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

EMBODIMENT OF FIGS. 1, 2 AND 3

Referring next to the drawings, a female urinary collection device of this invention is illustrated. In FIG. 1, the outer side view of the device is seen. This view of FIG. 1 is substantially full scale, with a molded cup-shaped receptacle or container 10, a very compliant rim portion 12 affixed to a top edge of the receptacle 10 and a discharge tube 14 which is secured within the receptacle 10.

Figure 2:
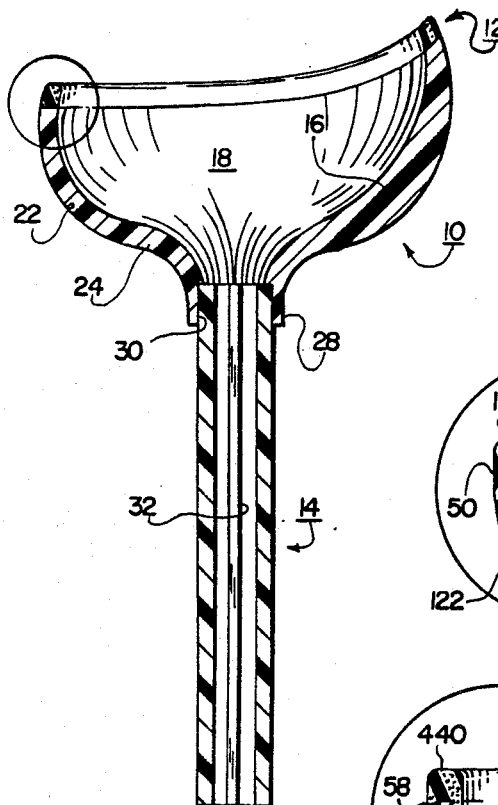
FIG. 2 represents a sectional side view of the collection device of FIG. 1 and showing the typical structure of this device, this view taken on the line 2—2 of FIG. 3 and looking in the direction of the arrows.
Figure 3:
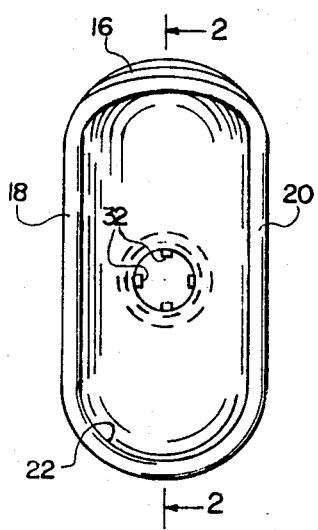
FIG. 3 represents a plan or top view of the device of FIG. 2 and looking downward from the open top toward and into the drainage tube portion.

In FIG. 2, the sectional side view of the device is depicted. The receptacle 10 is molded in and with a general saddle-shape. In the top view as seen in FIG. 3, the general configuration as depicted is avoid or may be elliptical. This receptacle 10 is made with a forward portion 16 which provides an upwardly-extending portion to conform to the front of the female anatomy. The side portions 18 and 20 are substantially symmetrically configured and in a convex arc sweep back to a rear portion 22 which is a more or less arcuate configuration. It is to be noted that these side and end portions of the receptacle are shaped and configured to produce a closed bowl shape 24 which terminates with an outlet stem portion 28 in which a stepped bore 30 is provided.

Secured in the stepped bore 30 is the discharge tube 14 preferably made of extruded tubing of flexible plastic. This tubing is formed with a plurality (four shown in FIG. 3) of inwardly-extending ribs or flutes 32 which are designed to prevent a shut-off developing when the tube 14 is bent into a pinch condition. The flutes 32 prevent any bending of and in the tube 14 from establishing a shut-off condition by a pinch fold. This inserted end of discharge tube 14 is secured as by adhesive, sonic welding or a heat seal. The extending portion of the tube 14 is flexible in the usual manner and is connected to another conductor and bag to be described in connection with FIG. 7 hereinafter.

EMBODIMENT OF FIG. 4A

Figure 4A:
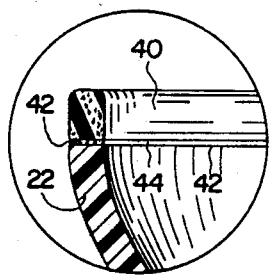

In FIG. 4A, the fragmentary view shows the rear portion 22 with a secured compliant rim identified as 40. This rim 40 is made to be secured to a top edge portion, identified as 42, of the receptacle 10. This edge portion is contemplated to be substantially the same width around all the essentially ovoid and convex extent. The compliant rim 40 is of soft foam, either of rubber, silicone rubber or plastic, having the composition of a material that does not take a permanent set and has substantial recovery so that resiliency is present at all times. The foam material selected and provided has a contact surface that has a softness which is non-irritating and deflects to the instant contact of and with the labia folds of the skin of the patient. The outwardly-facing surface of rim portion 40 is preferably slightly rounded to present a smooth contacting surface against the skin of the patient. A thin layer or film of adhesive 44 is indicated and is utilized to secure this rim portion 40 to the edge 42.

EMBODIMENT OF FIG. 4B

Figure 4B:
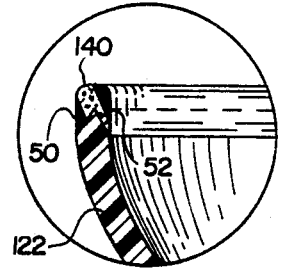

In FIG. 4B, there is depicted a fragmentary view similar to the showing in FIG. 4A, but with the rim portion made with a V-shaped seating surface. The rear portion of the receptacle is identified as 122 and the top edge of this molded receptacle is formed with a male V-shape protrusion 50. The compliant rim portion 140 is formed with a mating female V-groove identified as 52. As in FIG. 4A, it is contemplated that the rim 140 is secured to the molded receptacle edge as by adhesive.

EMBODIMENT OF FIG. 4C

Figure 4C:
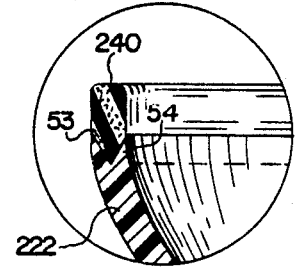

In the fragmentary and enlarged view of FIG. 4C, there is shown the configuration of FIG. 4B but with the V-shape alignment means in a reverse condition. The resilient compliant rim member is identified as 240, with this foam rim portion having a male V-shape protrusion 53 as an integral portion thereof. The outer lip edge of the molded receptacle has the upper wall identified as 222, formed with a female groove 54 sized and adapted to mate with the male protrusion 53 of the rim 240. Adhesive is contemplated to be used to make a securing of this rim 240 to the wall portion 222.

EMBODIMENT OF FIG. 4D

Figure 4E:
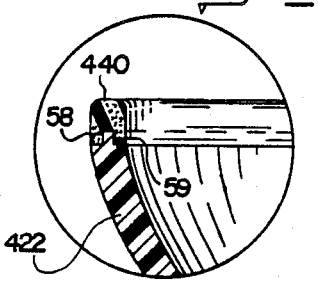
Figure 4D:
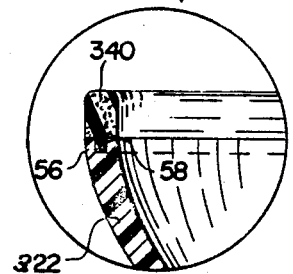

In the fragmentary and enlarged view of FIG. 4D, an alternate alignment means is shown. A foam rim portion, identified as 340, is depicted with an extending tenon portion 56 which, in the shape of tenons, is formed with a larger outer extent than the stem portion adjacent the rim portion. The outer wall portion 322 of this receptacle has its outer lip edge formed with a mortise groove 57 sized and adapted to receive and retain the tenon portion 56 of the rim 340.

EMBODIMENT OF FIG. 4E

In FIG. 4E, the view of FIG. 4D is depicted, but rather than the mortise and tenon of FIG. 4D this fragmentary view shows a reverse arrangement in which the foam rim portion, identified as 440, is formed with a mortise groove 58. The outer lip edge of the receptacle wall, identified as 422, is formed with a protruding tenon-shaped member 59. The tenon 59 is sized and adapted to be a snug fit in the mortise groove 58 in the resilient rim member 440.

EMBODIMENT OF FIG. 4F

Figure 4F:
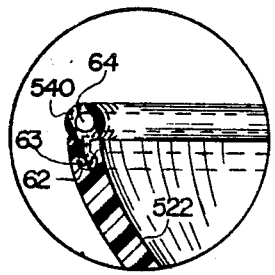

Referring next to the fragmentary enlarged sectional view as seen in FIG. 4F, the resilient rim portion is identified as 540 and has a protruding bead formed and extending downwardly therefrom. The lip edge of the receptacle has a wall 522 in which is formed a circular groove 62 sized to receive and retain the bead 63 provided on and extending from rim 540. The outer portion of this rim is generally circular in configuration and, if and when desired, is made hollow with an aperture 64 therein and therealong. This aperture or hole makes the rim 540 more compliant.

EMBODIMENT OF FIG. 4G

Figure 4G:
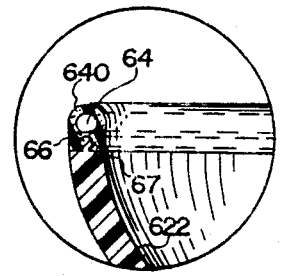

In FIG. 4G is shown an alternate or reverse retaining means from that shown in FIG. 4F. In this fragmentary, enlarged sectional view, the lip-edge of the wall, identified as 622, has a male protruding bead 66. A resilient, compliant rim portion 640 has a circular groove 67 which is sized and positioned to receive and retain the male protruding bead 66. As in FIG. 4F, the rim portion 640 may have an aperture 64 therethrough.

In the embodiments of FIGS. 4B through 4G, it is anticipated that adhesive be used to insure that accidental dislodgement does not intentionally or unintentionally occur. The several enlarged views indicate that preferably the rim portion may be an extrusion and then cut to length. Instead of the mortise and tennon arrangement of FIGS. 4D and 4E, there may be utilized a tongue-and-groove configuration or a plurality of mating protrusion portions and mating grooves, if desired, may be formed.

USE OF COMPLIANT RIM OF FIGS. 4A THROUGH 4G

The soft, compliant rim shown as attached to the upper edge of the receptacle is provided to insure that the use of this device is as comfortable as possible, does not irritate, and does not leak. The wearing of incontinent device is desirably as inconspicuous as possible. The device of this invention is made as small as practical. The soft, compliant rim, no matter the shape and means of attachment, is made sufficiently in extent that small changes in the labia conformation are accommodated. It is realized that this labia area is very tender and sensitive, but is conditioned to exposure of "wet" (urine) presence. These compliant rims are smooth so as to prevent any and all irritating conditions.

EMBODIMENT OF FIGS. 5 AND 6

It is contemplated that the device of FIG. 2 may be provided with a very thin liner 74 which is adapted to prevent urine from permeating a foam resilient rim portion 12. The resilient rim and the molded receptacle, with the change of the liner, enable the useful life of the device to be extended since urine does not readily come into contact with it. Without such liner, the compliant foam rim portion is continually subjected to urine which, in turn, permeates a portion of the wall and after a period of time emits an odor. With the liner in position, the device is generally identified as 110. The liner is made of impervious and very thin, flexible plastic such as Saran, polyethylene or like films. Such films are very thin and adhesive may be provided to assist in retention in the receptacle. It is to be noted that this liner 74 is brought over the resilient rim portion 12 to exclude any penetration thereof by urine from the patient. Conventionally, the liner may not be provided as the manufacture and sale of the device is sufficiently economical to encourage the use of a new device, as in FIG. 1, every two or three weeks.

EMBODIMENT OF FIG. 7

Referring next, and finally, to FIG. 7, there is depicted a retained female collection device as used by a patient 78. As depicted, an elasticized panty-like garment 80, which is a snug but not uncomfortable article of wearing apparel, provides the retention means. This panty-like garment is 80 and is made with a reinforced opening 82 which provides a guideway and support for tube 14 as it exits the reinforced opening. An additional convenient and conventional length of tubing 84 is connected to the tubing portion 14. To prevent air binding in this discharge conductor there is provided and depicted an air vent 86.

From this vent 86, a flexible tubular conductor 88 is shown as leading to a collection container 90 of conventional construction, which container may be secured to a leg by a suitably provided harness 92.

The use of the female collection device, described above in detail, anticipates a comfortable wearing of the device and, for this reason, the elasticized panty-like apparel 80 is utilized rather than a strap-like harness. The elasticized garment provides extended wearing of the device in comfort and security. The reinforcing of the opening 82 enables the garment to be washed and reused many times while providing a securing means for the device. The device with the compliant rim is retained in the fold area of the labia by the elasticized garment which presses the device into the placed position. The constant pressing force of garment 80, although light, causes irritation unless the rim 12 is very soft. For this reason, the device shown and described above anticipates a soft foam rim portion allowing wearing of the device without irritation and providing a leak-free condition and position. This retention arrangement permits the user to be ambulatory and the wearing is inconspicuous.

The rim portion 12 is made of a compliant foam which is secured to the receptacle 10 at its upper and outer edges. This foam may be extruded as silicone foam rubber or may be from molded configurations of rubber and/or plastic. The securing garment 80 may be a panty-girdle conventionally made with an elasticized front panel. The aperture for the tubular member 14 is made with a reinforcement 82 to prevent undue wear and raveling from a strain which tends to develop a tearing action. This reinforcement provides an extension of the life expectancy. The receptacle 10 is anticipated to be a molded member such as plastic, which is an inexpensive material and is quite predictable in its characteristics. Other materials such as rubber, silicone rubber and combination materials may be used also. An extruded foam of silicone rubber having a reading of approximately thirty-five on a Durometer scale "A" has been found to be satisfactory. This noting of alternate materials and degrees of softness is not to preclude other materials which may be developed and prove to be more economical and/or satisfactory. The rim material of this invention must be soft, compliant and non-irritating when brought to the fold area of the user's labia and for the expected periods of use.

In the drawings, several configurations of rim- and edge-securing and -aligning have been shown, but these are only illustrative of the many ways of establishing an alignment of the rim with the lip-edge. The particular molding technique will establish the configuration or configurations used, and modifications are contemplated to accommodate manufacturing equipment.

Molding techniques are constantly improving and the materials used therewith and therein are also constantly changing, so this concept is intended to include the making of the female urinary collection device of FIGS. 1 and 2 as a unitary molding of the cup and rim from a material such as closed-cell silicone foam. The configuration and size is a matter of selection, as described above, but the making of a molding with a soft, compliant rim portion is also contemplated. Economics is a great consideration as this collection device is subject to replacement within a few days or weeks. The soft, compliant rim portion is brought into contact with the fold area of the user's labia so comfort and compliance is a must.

The collection device is adapted to be brought into a leak-free position and condition in the folds of the user's labia when held by a worn retaining-assist.

The initial collector receptacle 10 is shown as ovoid, but this is merely a matter of preference as any elliptical shape may also be provided. It is contemplated that this receptacle be molded as this is an economical means of supplying a plastic member. The cup-shaped receptacle may also be a pressure-shaped unit or thermoformed. The receptacle 10 is contemplated as being slightly resilient as a matter of wearing comfort. The use of a separate tubing extent 14 is a matter of preference as the extent of tubular conducting means is also a matter of preference. The conductor is preferably made of extruded tubing and connection means is also well known. The rim foam is depicted in several shapes but, whatever the shape, the foam is sufficiently soft to prevent irritation to the skin area of the folds of the labia of the female user. Since users may have differing degrees of sensitivity, the rims are not only shown with differing means of attachment but also may be of selected softness and thickness. The receptacle 10 is shown in FIG. 3 with essentially parallel side walls, but this is only a preferred configuration. The receptacle is made as small and unobtrusive as practical. The vent 86 is shown intermediate the discharge end of tubing 14 and receptacle 90, but the positioning of the vent is a matter of choice as the purpose of the vent is to prevent air binding of fluid flow and enable all discharged urine to readily flow to the receptacle 90. This receptacle 90 may be reused after emptying or a new and like unit may be utilized as preferred.

As noted above, the molding may be unitarily provided, but a soft, compliant rim is required for the comfort of the user. A unitary molding may enable the size of the receptacle to be made smaller and more comfortable. Size and weight is a criteria of the commercial acceptance of the device.

What is claimed is:

1. An incontinent female collection device including
a receptacle of a generally ovoid and open cup-shaped configuration providing a cavity with an open bore from and through a wall portion of said cavity;
an outer lip-edge formed on said open cup-shaped receptacle, said lip-edge providing a generally ovoid saddle-shape configuration;
a resilient, soft, compliant outer-rim portion extending around the full perimeter of said lip-edge, said rim portion being comprised of a material which provides for deflection and compression of said rim portion so as to accommodate individual female anatomical differences in and of the skin area of the folds of the user's labia and in a wet environment;
means for securing said rim portion to said lip-edge of said receptacle so that a fluid-tight seal therebetween is established and maintained;
a very thin liner of very flexible plastic film secured to the outer surfaces of said rim portion and lying adjacent at least the upper portion of the inner surface of said cup-shaped receptacle; and
means for attaching said collection device to a conduit and collection container.

2. An incontinent female collection device as in claim 1 in which the very thin liner is attached by adhesive means to the resilient, soft, compliant rim portion to provide protection of said rim from contact by urine.

3. An incontinent female collection device comprising a receptacle having a generally ovoid and open cup-shaped configuration to provide a cavity, said receptacle including an outer edge portion having a saddle-shape to conform to a female user's anatomy and an outlet stem portion;

a resilient compliant rim portion affixed to said outer edge portion of said receptacle for placement in the folds of a female user's labia, said rim portion having a softness which permits deflection to an instant contact with the labia folds of a female user; and a liner of plastic film secured over said rim portion to protect said rim portion from contact with urine.

4. An incontinent female collection device comprising a receptacle having a generally ovoid and open cup-shaped configuration to provide a cavity, said receptacle including an outer edge portion having a saddle-shape to conform to a female user's anatomy and an outlet stem portion;

a resilient compliant rim portion affixed to said outer edge portion of said receptacle for placement in the folds of a female user's labia, said rim portion having a softness which permits deflection to an instant contact with the labia folds of a female user and being sufficiently narrow to provide comfortable engagement with the folds of the labia of the user; and said receptacle and rim portion being of a closed-cell foam silicone material having a durometer of about 35 on the A-Shore scale.

5. A device as set forth in claim 4 which further comprises a discharge tube secured within said outlet stem portion and having inwardly extending ribs to prevent a shut-off of said tube when bent.

6. A device as set forth in claim 5 further comprising a container in communication with said tube to receive discharged urine and a vent means between said tube and said container for preventing blockage of the fluid flow to said container.

7. A device as set forth in claim 4 wherein said receptacle is a unitary molding of slightly deformable material.

8. A device as set forth in claim 4 further comprising a layer of adhesive securing said rim portion to said outer edge portion of said receptacle.

9. A device as set forth in claim 4 wherein said outer edge portion has a protrusion and said rim portion has a mating groove receiving said protrusion.

10. A device as set forth in claim 4 which further comprises a mortise and tenon arrangement for affixing said rim portion to said outer edge portion.

11. A device as set forth in claim 4 wherein said outer edge portion has a groove of circular shape and said rim portion has a protruding bead received in said groove.

12. A device as set forth in claim 11 wherein said rim portion has a hollow outer portion.

13. A device as set forth in claim 4 wherein said outer edge portion has a protruding bead and said rim portion has a circular groove receiving said bead.

14. A device as set forth in claim 4 wherein said receptacle has an upwardly extending forward portion to conform to the front of the female anatomy.

15. A device as set forth in claim 4 in which said receptacle is integrally molded, with said rim portion sufficiently narrow to be deformed easily, and with said receptacle having thicker cross-sectioned walls than said rim portion to provide a stiffer portion.

* * * * *

UNITED STATES PATENT AND TRADEMARK OFFICE
CERTIFICATE OF CORRECTION

PATENT NO. : 4,904,248

DATED : February 27, 1990

INVENTOR(S) : VINCENT L. VAILLANCOURT

It is certified that error appears in the above-identified patent and that said Letters Patent is hereby corrected as shown below:

Column 1, line 66 "commerically" should be --commercially--

Column 3, line 13 "complaint" should be --compliant--

Signed and Sealed this

Fourteenth Day of May, 1991

Attest:

HARRY F. MANBECK, JR.

*Attesting Officer*     *Commissioner of Patents and Trademarks*